United States Patent [19]
Grundy et al.

[11] Patent Number: 5,352,840
[45] Date of Patent: Oct. 4, 1994

[54] OXIDATION PROCESS

[75] Inventors: Stephen G. Grundy, Widnes; Kevan M. Reeve, Liverpool; Michael C. Rocca, Manchester, all of England

[73] Assignee: Solvay Interox Limited, Warrington, England

[21] Appl. No.: 59,157

[22] Filed: May 10, 1993

[30] Foreign Application Priority Data

May 9, 1992 [GB] United Kingdom ................. 9210027

[51] Int. Cl.$^5$ ...................... C07C 45/27; C07C 45/30
[52] U.S. Cl. .................... 568/430; 568/420; 568/426
[58] Field of Search ................ 568/426, 420, 430

[56] References Cited
U.S. PATENT DOCUMENTS 4,480,135  10/1984  Esposito et al. .................... 568/430

Primary Examiner—Werren B. Lone
Attorney, Agent, or Firm—Larson and Taylor

[57] ABSTRACT

Substituting aqueous hydrogen peroxide/hydrogen bromide for bromine in a known process for producing a ditertiaryalkyl substituted hydroxybenzaldehyde such as ditertiarybutyl hydroxybenzaldehyde from the corresponding ditertiaryalkyl substituted methylphenol results in a substantially impaired yield of product.

Improved yields are obtained by employing a reaction temperature of at least 40° C., preferably 50° to 80° C. in conjunction with a hydrophobic solvent such as chloroform. Preferably, the process employs very concentrated hydrogen peroxide solution, 65% to 75% w/w, introduced into the bromide-containing reaction mixture during a period of from 25 to 75 minutes.

10 Claims, No Drawings

OXIDATION PROCESS

The present invention relates to an oxidation process and more particularly relates to a process for selectively producing a dialkylsubstituted hydroxybenzaldehyde from a dialkylsubstituted methylphenol.

3,5-ditertiaryalkyl-4-hydroxybenzaldehyde compounds are desirable as intermediates in pharmaceutical or agrochemical production, and particularly the tertiary butyl compounds. Coppinger and Campbell have proposed in JACS vol 75, i 1953, p734–736, to obtain such products by reacting the corresponding 2,6-ditertiary alkyl-4-methylphenol with bromine in an alcoholic solvent, specifically t-butanol, at 25° C. Although the process produces the desired product effectively, it suffers inherently from the two principal difficulties or disadvantages associated with the use of bromine as primary reagent which arise from its hazardous, toxic nature. Consequently, there are restrictions upon the manner of its use and constraints upon the disposal of effluents or residues containing its derivatives.

In recent years, a team of research chemists at Interox Chemicals have developed processes for replacing bromine as the primary reagent in organic syntheses, including, in particular, processes for the side chain oxidation of alkyl substituents of aromatic compounds, as described, for example, in U.S. Pat. No. 4923580, U.S. Pat. No. 4,943,358 and U.S. Pat. No. 5,092,971. In such processes, the primary reagents were hydrogen peroxide and bromide ions, thereby circumventing or at least diminishing the handling and waste disposal problem of bromine and in many instances the reaction was conducted photolytically.

The Interox team sought to substitute hydrogen peroxide/hydrogen bromide for bromine in the process described by Coppinger and Campbell, but found that by so doing, the yield of the desired aldehyde product was virtually halved and the conversion of the substrate was also lower. Accordingly, they recognised that if they were to employ hydrogen peroxide/hydrogen bromide instead of bromine, they needed to devise a variation which would ameliorate the reduction in yield of aldehyde.

One factor which is known to affect the rate and/or extent of a chemical reaction is the temperature at which it is conducted and in general, the rate is expected to increase with increasing temperature. However, when the substitute Coppinger/Campbell process employing peroxide/bromide was repeated at a higher temperature, 60° C., which would be expected to accelerate the reaction, it was found that the conversion of the substrate was little changed, but that a very substantial change had arisen in aldehyde production. Far from improving its production, the increase in temperature had resulted in a yield of only 1% aldehyde.

In a second variation of the Coppinger/Campbell conditions, a hydrophobic solvent was employed together with bromide/peroxide at their reaction temperature, i.e. 25° C. instead of the hydrophilic butanol solvent, but the net result was once again a very low yield of aldehyde.

Thus, to summarise, a simple substitution of peroxide/bromide for bromine in the Coppinger/Campbell gave a poor yield of aldehyde and the two variations tested, i) increasing the reaction temperature and ii) changing the reaction solvent, each resulted in a significant reduction of the yield of aldehyde product, thereby indicating that neither of them represents a means to attain the objective of substituting bromide/peroxide for bromine.

It is an object of the present invention to devise a process for the production of substituted benzaldehydes employing hydrogen peroxide and bromide that ameliorates or overcomes the above-identified difficulties.

According to the present invention, there is provided a process for the production of a 3,5-ditertiaryalkyl-4-hydroxybenzaldehyde from a 2,6-ditertiary alkyl-4-methylphenol by reaction with aqueous hydrogen bromide and hydrogen peroxide characterised by conducting the reaction in the presence of a hydrophobic solvent at a reaction temperature selected between 40° C. and the boiling point of the reaction mixture.

Surprising, despite the observation that each of the variations of increasing reaction temperature and changing the solvent impaired the yield of aldehyde product, the combination of the two variations increased the yield.

The process is particularly applicable to the conversion of tertiary alkyl substituted methylphenol compounds in which each of the two tertiary alkyl substituents satisfies the formula:

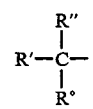

in which at least one and preferably at least two of R°, R' and R" represent a methyl and the total number of carbons in the substituent is from 4 to 10. The tertiary alkyl substituent is especially tertiary butyl. Both tertiary alkyl substituents can be the same or can be different.

The hydrophobic solvents in which the process of the present invention is conducted are often selected from either hydrocarbons or chlorinated hydrocarbons which are liquid at ambient temperature and which have a boiling point that is not lower than about 50° C. Such solvents include chloroform or dichloromethane, and chlorinated low molecular weight C2 to C4 hydrocarbons, such as ethylenedichloride, tetrachloroethane, trichloroethane or dichloropropane. Such solvents permit the reaction to be conducted at above 40° C. and most permit reaction in the preferred temperature range of from about 50° C. to about 80° C.

It is desirable to employ a mole ratio of at least 1.5 moles of hydrogen peroxide per mole of substrate, and preferably sufficient to permit approximately 2 moles or more of bromine to be generated during the course of the reaction. Usually, the mole ratio selected is less than 3:1. In many practical instances, the mole ratio peroxide:substrate is selected in the region of from about 1.8:1 to about 2.5:1.

It is highly desirable to introduce the hydrogen peroxide solution into the reaction mixture in the form of a concentrated solution, such as of at least 30% w/w and preferably at least 45% w/w. In order to improve the yield of aldehyde product, it is preferable to introduce the hydrogen peroxide solution at a higher rather than a lower concentration and most advantageous to employ the highest concentration available. Practical supply considerations dictate that the solution is unlikely to contain greater than about 85% w/w hydrogen peroxide, and indeed the more commonly available material has a concentration in the range of about 65 to about 75% w/w.

It is desirable to introduce the hydrogen peroxide solution progressively into the reaction mixture, often during a period of at least 20 minutes up to about 4 hours, in many embodiments selected in the range of about 25 minutes to about 150 minutes and in some preferred embodiments in the range of from 25 to 75 minutes.

The overall reaction is believed to include the steps of bromine generation by reaction between hydrogen peroxide and bromide, bromination of the substrate and subsequently bromide elimination from the substrate, such as by hydrolysis. During such a process sequence, bromide is regenerated. Consequently, it is possible to employ less than a stoichiometric amount of bromide in the reaction mixture, i.e. less than 4 moles per mole of substrate. It is desirable to employ a mole ratio of bromide:substrate of at least 1.5:1 and preferably from about 2:1 to about 3:1. It is usually present in an aqueous phase in the reaction mixture and preferably at a concentration in the aqueous phase of not lower than 15% w/w and especially is greater than about 30% w/w. In most embodiments, all the bromide solution is present when introduction of hydrogen peroxide commences.

The hydrophobic solvent and aqueous phases are often present in a volume ratio of at least 1:1 approximately, and the ratio is, in many instances, not greater than about 5:1.

The reaction period is normally selected in the range of from about 1 hour to about 10 hours and particularly from about 1.5 hours to about 5 hours, calculated from the time when hydrogen peroxide introduction to a bromide-containing reaction mixture commences. In practice, the period usually includes a post peroxide addition period of from about 1 hour to about 5 hours to permit the later stages of the reaction process to continue.

The reaction is advantageously conducted in the absence of illumination that is capable of dissociating bromine molecules into free radicals, for example light having a wavelength shorter than about 600 nm such as from about 250 to 600 nm, although the reaction can tolerate such illumination to some extent. Such antipathy towards bromine-dissociating irradiation distinguishes the present invention oxidation process from many apparently related reactions involving bromination of an alkyl substituent of an aromatic nucleus that require photolytic conditions.

At the end of the reaction period, the reaction mixture is permitted to cool or cooled, preferably to below ambient temperature, such as from about 5° to about 10° C., which encourages a solid product, the desired aldehyde, to precipitate. The precipitate can be separated from the supernatant liquor by conventional separation techniques including centrifugation and filtration.

Having described the invention in general terms, specific embodiments thereof will now be described more fully by way of example only.

Comparisons CA to CD and Examples Ex1 to Ex5
In Comparisons CB to CD and the Examples, 2,6-di-t-butyl-4-methylphenol (11 g, 0.05 mol), aqueous hydrobromic acid solution (48% w/w, 17.9 g, 0.106 mol) and solvent (50 g) were charged into a 100 ml round bottomed flask fitted with a thermocouple controlled bottom heater, an inlet port for the aqueous hydrogen peroxide solution, a mechanical stirrer and water-cooled condenser. The flask was warmed, where necessary, to the reaction temperature and then maintained at that temperature whilst an aqueous hydrogen peroxide solution (70% w/w, 4.9 g, 0.1 mol) was introduced, over a period of 2 hours except in Example 4 where it was 1 hour. After a total reaction period of 4 hours at the same temperature, the mixture was cooled to approximately 5° C., and a precipitate was observed which was separated from the mother liquor by filtration. The filter cake was water washed, dried and analysed by hplc.

In Comparison A, the procedure of Comparison B was followed, except that liquid bromine, 0.1 mol, was employed instead of both the hydrobromic acid and hydrogen peroxide solutions.

In Example 2, the procedure of Example 1 was varied by conducting the reaction in a darkened vessel, and in Example 4, the procedure of Example 1 was varied by maintaining the reaction mixture at its reaction temperature for an additional 2 hours. In Example 5, the procedure of Example 1 was varied by introducing 35% w/w solution of hydrogen peroxide, 9.8 g, 0.1 mol, instead of the 70% w/w solution.

The process conditions and results are summarised in the Table below.

The Table

| Comp/Example | Solvent | Reaction Temperature °C. | Substrate Converted % | Yield of Aldehyde % |
|---|---|---|---|---|
| Comp A | t-butanol | 25 | 100 | 94 |
| Comp B | " | 25 | 77 | 50 |
| Comp C | " | 60 | 73 | 1 |
| Comp D | chloroform | 25 | 98 | 31 |
| Ex 1 | " | 60 | 98 | 81 |
| Ex 2 | " | 60 | 97 | 74 |
| Ex 3 | " | 60 | 100 | 70 |
| Ex 4 | " | 60 | 96 | 84 |
| Ex 5 | " | 60 | 98 | 64 |

From the Table above, and particularly by comparing Comparisons A, B, C and D with each other, it can be seen that the use of hydrogen peroxide/hydrogen bromide instead of bromine impaired the conversion to the desired aldehyde product, and that further impairment was observed by either varying the reaction temperature or the organic solvent. However, by comparing Example 1 with comparison B, it can be seen that a substantial improvement in yield of the desired aldehyde was achieved by changing both the temperature and the solvent in concert, even though changing each of them alone had impaired the yield.

Comparison between Examples 4 and 1 demonstrate that increasing the rate of introductionOn of the hydrogen peroxide at the early part of the reaction period enhanced the yield of aldehyde, and a comparison of Examples 1 and 5 demonstrate that the use of 70% hydrogen peroxide solution is preferable to 35% solution.

We claim:
1. A process for the production of a 3,5-ditertiaryalkyl-4-hydroxybenzaldehyde from a 2,6-ditertiary alkyl-4-methylphenol by reaction with aqueous hydrogen bromide and hydrogen peroxide characterised by conducting the reaction in the presence of a hydrophobic solvent at a reaction temperature selected between 40° C. and the boiling point of the reaction mixture.

2. A process according to claim 1 characterised in that each of the two tertiary alkyl substituents satisfies the formula:

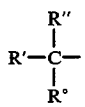

in which at least one and preferably at least two of R°, R' and R" represent a methyl and the total number of carbons in the substituent is from 4 to 10.

3. A process according to claim 1 or 2 characterised in that the tertiaryalkyl substituent is tertiary butyl.

4. A process according to claim 1 or claim 2 characterised in that reaction is conducted at a temperature of from 50° to 80° C.

5. A process according to claim 1 or claim 2 characterised in that the hydrophobic solvent is a chlorinated hydrocarbon having a boiling point of at least 50° C.

6. A process according to claim 1 or claim 2 characterised in that the hydrogen peroxide solution employed has a concentration of from 65% to 75% w/w.

7. A process according to claim 1 or claim 2 characterised in that hydrogen peroxide is employed in a mole ratio to the substrate of from about 1.8:1 to about 2.5:1.

8. A process according to claim 1 or claim 2 characterised in that the hydrogen peroxide solution is introduced progressively into the reaction mixture over a period of from 25 to 75 minutes.

9. A process according to claim 1 or claim 2 characterised in that bromide is employed in a mole ratio to the substrate in the range of from about 2:1 to about 3:1.

10. A process according to claim 1 or claim 2 characterised in that the reaction is conducted in the substantial absence of bromine-dissociating illumination.

* * * * *